(12) United States Patent
Carlino et al.

(10) Patent No.: US 12,059,347 B2
(45) Date of Patent: Aug. 13, 2024

(54) TILTABLE TOOLS FOR HEART VALVE PROSTHESIS

(71) Applicant: Corcym S.r.l., Milan (IT)

(72) Inventors: Felice Giuseppe Carlino, Saluggia (IT); Monica Francesca Achiluzzi, Saluggia (IT)

(73) Assignee: Corcym S.r.l., Milan (IT)

( * ) Notice: Subject to any disclaimer, the term of this patent is extended or adjusted under 35 U.S.C. 154(b) by 814 days.

(21) Appl. No.: 17/254,179

(22) PCT Filed: Aug. 6, 2018

(86) PCT No.: PCT/IB2018/055890
§ 371 (c)(1),
(2) Date: Dec. 18, 2020

(87) PCT Pub. No.: WO2020/030944
PCT Pub. Date: Feb. 13, 2020

(65) Prior Publication Data
US 2021/0259834 A1    Aug. 26, 2021

(51) Int. Cl.
*A61F 2/24* (2006.01)
(52) U.S. Cl.
CPC .................. *A61F 2/2427* (2013.01)
(58) Field of Classification Search
CPC ..... A61F 2/2427; A61F 2/2466; A61F 2/2496
See application file for complete search history.

(56) References Cited

U.S. PATENT DOCUMENTS 5,735,842 A * 4/1998 Krueger ................ A61F 2/2427
606/1
5,788,689 A * 8/1998 Allan .................... A61F 2/2427
606/1
(Continued)

FOREIGN PATENT DOCUMENTS

DE    202011000848 U1    6/2011
EP       0095970 A2    12/1983
(Continued)

OTHER PUBLICATIONS

International Preliminary Report on Patentability received for PCT Patent Application No. PCT/IB2018/055890, dated Feb. 18, 2021, 9 pages.
(Continued)

*Primary Examiner* — Sarah W Aleman
(74) *Attorney, Agent, or Firm* — Eversheds Sutherland (US) LLP; Christopher C. Bolten; Albert K. Heng

(57) ABSTRACT

In certain embodiments, an implantation accessory for placement at a heart valve annulus location of a patients heart, the annulus having a first axis, the implantation accessory comprising: a first surface; a second axis perpendicular to the first surface; and, a maneuvering system for aligning the first axis and the second axis. In certain embodiments, a removable bioprosthetic heart valve assembly for implantation into an abutment ring attached at a heart valve annulus location of a patients heart, the abutment ring having a first axis, the removable bioprosthetic heart valve assembly includes a bioprosthetic valve for coupling to the abutment ring and a holder. The holder, detachably coupled to the bioprosthetic valve, includes a first surface, a second axis perpendicular to the first surface, and a maneuvering system for aligning the first axis and the second axis. Methods of implantation are also disclosed.

20 Claims, 14 Drawing Sheets

(56) References Cited

U.S. PATENT DOCUMENTS

| | | | | |
|---|---|---|---|---|
| 5,972,030 | A | * | 10/1999 | Garrison .......... A61B 17/06061 |
| | | | | 623/2.11 |
| 2009/0093877 | A1 | * | 4/2009 | Keidar ................ A61F 2/2427 |
| | | | | 623/2.11 |
| 2015/0327998 | A1 | | 11/2015 | Keidar et al. |
| 2017/0020527 | A1 | * | 1/2017 | Williams ........... A61B 17/1155 |
| 2018/0116795 | A1 | * | 5/2018 | Conklin ............... A61F 2/2427 |

FOREIGN PATENT DOCUMENTS

| | | |
|---|---|---|
| EP | 3034014 A2 | 6/2016 |
| JP | 2004154164 A | 6/2004 |
| WO | WO-2010112608 A1 | 10/2010 |
| WO | 2017/216607 A1 | 12/2017 |

OTHER PUBLICATIONS

International Search Report and Written Opinion received for PCT Patent Application No. PCT/IB2018/055890, dated Apr. 1, 2019, 11 pages.

* cited by examiner

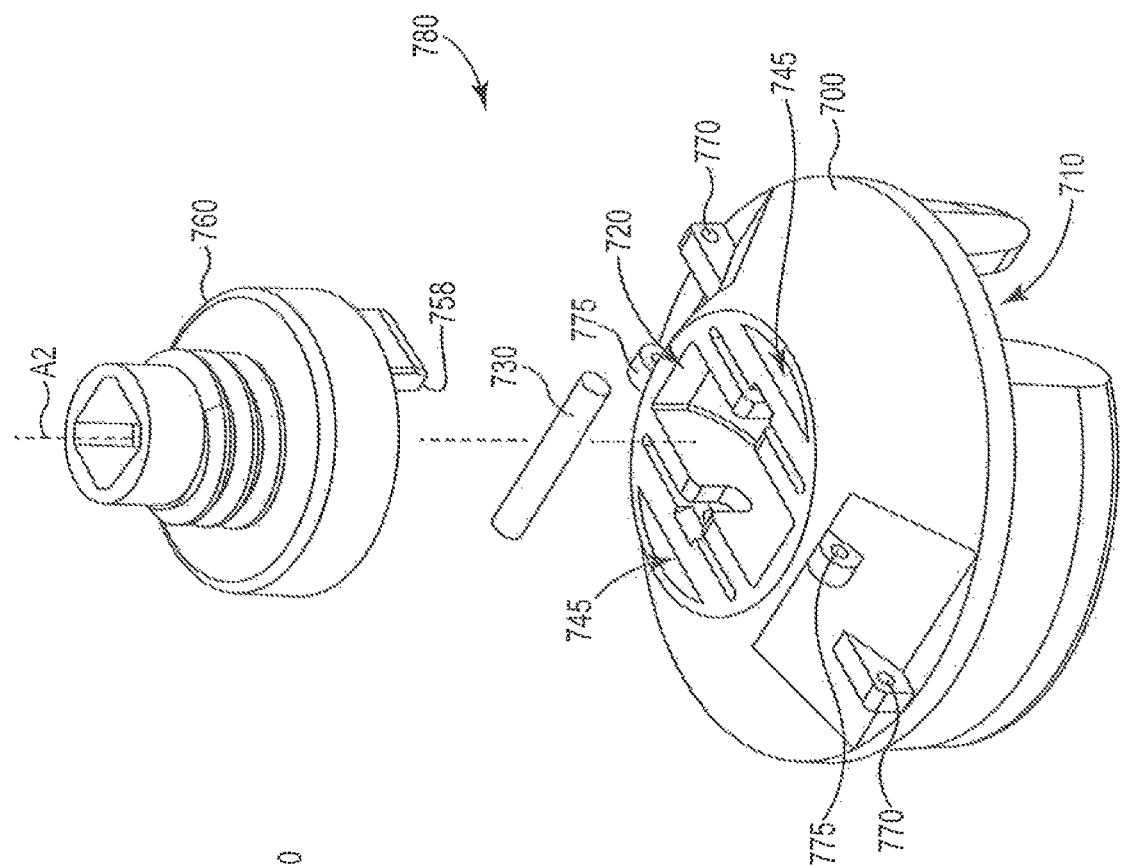
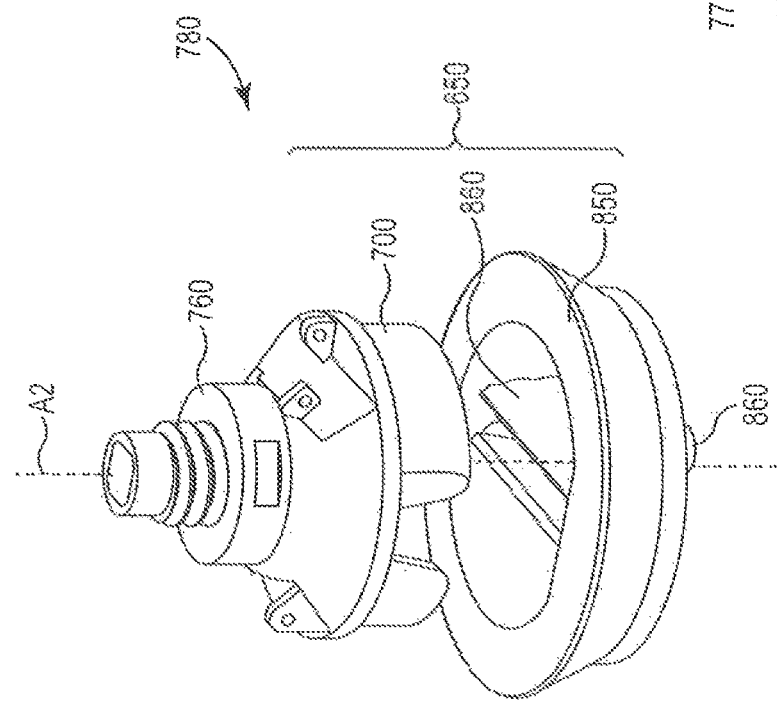
FIG. 8B
FIG. 8A

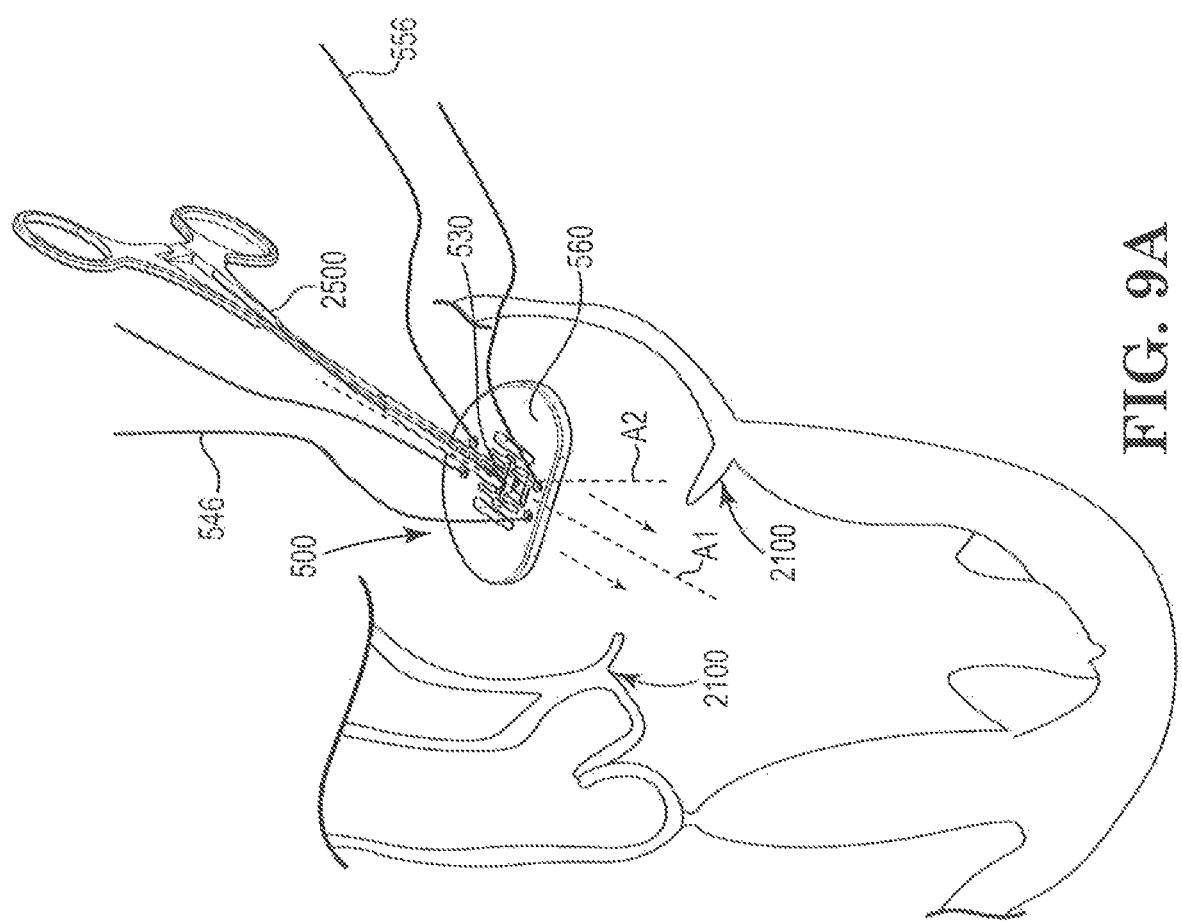

TILTABLE TOOLS FOR HEART VALVE PROSTHESIS

CROSS REFERENCE TO RELATED APPLICATIONS

This application is a national stage application of PCT/IB2018/055890 filed Aug. 6, 2018, which is herein incorporated by reference in its entirety.

TECHNICAL FIELD

The present disclosure relates generally to a prosthetic mitral valve, implantation accessories, and associated implant methods.

BACKGROUND

Prosthetic heart valves can replace defective human valves in patients. Prosthetic heart valves come in two varieties: bioprosthetic (e.g., tissue) heart valves and mechanical heart valves. During a valve replacement procedure, valve prostheses are typically sutured to peripheral tissue of a natural heart valve orifice (the "annulus") after surgical removal of damaged or diseased natural valve structure. For example, the sewing ring of the prosthetic valve may be secured to the annulus via sutures. This procedure can be very complicated, as surgeons are manipulating multiple sutures and small components while working in tight spaces with limited visibility. The difficulties can be even greater with the implementation of tissue valves, given their shape and construction.

When placing a bioprosthetic heart valve in a mitral position, for example, the commissure posts are the first portion of the valve entering inside the patient's annulus during valve delivery. Given the close proximity of the multiple pre-installed sutures and the commissure posts, it is not uncommon for one or more of the commissure posts to become entangled with one or more of the pre-installed sutures (commonly referred to as "suture looping"). Moreover, as the commissure posts are not visible at this point during the procedure, the surgeon cannot visually detect whether any such entanglement has occurred. This problem is even more pronounced during a minimally-invasive access approach, a technique that is quickly becoming more common in the industry, which provides even more limited visibility of the surgical field during valve delivery.

Prosthetic heart valves are often implanted using minimally invasive cardiothoracic surgery (MICS) tools and techniques. MICS techniques involve performing a procedure or implanting a device through a small incision (e.g., often through the ribs), so require tools allowing access to the cardiothoracic region through this smaller incision. There is a need for implantation accessories, systems and methods to efficiently size and align the valve for ease of implantation.

SUMMARY

Example 1 is an implantation accessory for placement at a heart valve annulus location of a patient's heart, the annulus having a first axis, the implantation accessory comprising: a first surface; a second axis perpendicular to the first surface; and, a maneuvering system for aligning the first axis and the second axis.

Example 2 is the implantation accessory according to Example 1, wherein the maneuvering system includes a central pin pivotable relative to the surface, and wherein the second axis is orthogonal to the central pin.

Example 3 is the implantation accessory according to either Example 1 or Example 2, wherein the maneuvering system includes a first threadable bore and a second threadable bore, each bore having first and second openings disposed at the first surface.

Example 4 is the implantation accessory according to any of Examples 1-3, wherein the first threadable bore and the second threadable bore include a first thread and a second thread therethrough, respectively, for tilting the first surface and aligning the first axis and the second axis.

Example 5 is the implantation accessory according to any of Examples 1-4, wherein the central pin is graspable to a minimally invasive cardiothoracic surgery (MICS) forceps.

Example 6 is the implantation accessory according to any of Examples 1-5, wherein the implantation accessory is configured to size the annulus.

Example 7 is the implantation accessory according to any of Examples 1-6, wherein the implantation accessory is configured to implant a removable bioprosthetic heart valve assembly.

Example 8 is the implantation accessory according to any of Examples 1-7, wherein the implantation accessory is configured to implant a removable mechanical heart valve assembly.

Example 9 is the implantation accessory according to any of Examples 1-8, wherein the implantation accessory is configured to position a plurality of leaflets of the removable mechanical heart valve assembly.

Example 10 of the present invention is a removable bioprosthetic heart valve assembly for implantation into an abutment ring attached at a heart valve annulus location of a patient's heart, the abutment ring having a first axis, the removable bioprosthetic heart valve assembly comprising: a bioprosthetic valve for coupling to the abutment ring; and, a holder detachably coupled to the bioprosthetic valve, the holder having: a first surface; a second axis perpendicular to the first surface; and, a maneuvering system for aligning the first axis and the second axis.

Example 11 is the removable bioprosthetic heart valve assembly of Example 10, wherein the maneuvering system includes a central pin pivotable relative to the holder, and wherein the second axis is orthogonal to the central pin.

Example 12 is the removable bioprosthetic heart valve assembly according to Example 11, wherein the central pin is further rotatable with the holder in a first clockwise direction and in a second counter-clockwise direction.

Example 13 is the removable bioprosthetic heart valve assembly according to any of Examples 10-12, wherein the maneuvering system includes a first threadable arcuate bore and a second threadable arcuate bore, each bore having first and second openings disposed at the first surface.

Example 14 is the removable bioprosthetic heart valve assembly according to Example 13, wherein the first threadable arcuate bore and the second threadable arcuate bore include a first thread and a second thread therethrough, respectively, for tilting the first surface and aligning the first axis and the second axis.

Example 15 is the removable bioprosthetic heart valve assembly according to any of Examples 10-14, further comprising a detachable fit joint having a proximal end and a distal end, the proximal end configured for coupling to the holder and the distal end configured for coupling to an elongated handle.

Example 16 is the removable bioprosthetic heart valve assembly according to any of Examples 10-15, further comprising the abutment ring, wherein the abutment ring includes a locking system and the bioprosthetic valve includes at least one locking feature, the at least one locking feature configured to be received by the locking system.

Example 17 is the removable bioprosthetic heart valve assembly according to Example 16, wherein the locking system comprises at least one channel configured to accept the at least one locking feature of the bioprosthetic valve such that the holder can be rotated relative to the abutment ring to at least a first engaged position and a second disengaged position.

Example 18 is the removable bioprosthetic heart valve assembly according to Example 17, wherein the maneuvering system includes a central pin rotatable with the holder relative to the abutment ring to rotate the holder in a first clockwise direction to the engaged position and in a second counter-clockwise direction to the disengaged position.

Example 19 is the removable bioprosthetic heart valve assembly according to any of Examples 16-18, wherein the abutment ring is attachable to a patient's mitral valve rim.

Example 20 is the removable bioprosthetic heart valve assembly according to any of Examples 11-12, wherein the central pin is graspable to a minimally invasive cardiothoracic surgery (MICS) forceps.

Example 21 is a method of implanting multiple component heart valve prosthesis, the method comprising: securing an abutment ring to a heart valve annulus of a patient's heart, the abutment ring having a first axis; advancing a removable bioprosthetic heart valve assembly adjacent to the abutment ring, the removable bioprosthetic heart valve assembly comprising a bioprosthetic valve for coupling to the abutment ring and a holder detachably coupled to the bioprosthetic valve, the holder having a first surface, a second axis perpendicular to the first surface, and a maneuvering system for aligning the first axis and the second axis; maneuvering the maneuvering system to align the first axis and the second axis; seating the bioprosthetic valve by further advancing the removable bioprosthetic heart valve assembly into the abutment ring; coupling the bioprosthetic valve to the abutment ring; and, removing the holder.

Example 22 is the method according to Example 21, wherein the maneuvering system comprises a central pin pivotable relative to the holder, the second axis orthogonal to the central pin, and wherein the step of maneuvering includes pivoting the central pin using an attachable minimally invasive cardiothoracic surgery (MICS) forceps.

Example 23 is the method according to Example 22, wherein the central pin is rotatable with the holder, and wherein the step of maneuvering includes rotating the holder in a first clockwise direction and in a second counter-clockwise direction.

Example 24 is the method according to any of Examples 21-23, wherein the maneuvering system comprises a first threadable arcuate bore and a second threadable arcuate bore, each bore having first and second openings disposed at the first surface and first and second threads disposed therethrough, and wherein the step of maneuvering includes pulling on the first and second threads to tilt the first surface and to align the first axis and the second axis.

Example 25 is the method according to any of Examples 21-24, wherein the removable bioprosthetic heart valve assembly further comprises a detachable fit joint having a proximal end and a distal end, the proximal end coupled to the holder and the distal end coupled to an elongated handle, and wherein the step of advancing further includes inserting the removable bioprosthetic heart valve assembly via the handle.

Example 26 is the method according to Example 25, wherein before the step of advancing the fit joint is detached to the elongated handle from the valve assembly.

Example 27 is the method according to any of Examples 21-26, wherein the abutment ring includes a locking system and the bioprosthetic valve includes at least one locking feature, the at least one locking feature configured to be received by the locking system, and wherein the step of seating the bioprosthetic valve to the abutment ring includes rotating the holder in the first clockwise direction to a first engaged position and in the second counter-clockwise direction to a second disengaged position.

Example 28 is a multiple component heart valve prosthesis for implantation at a heart valve annulus location of a patient's heart, the heart valve prosthesis comprising: an abutment ring configured for attachment at the heart valve annulus location, the abutment ring having a first axis; and a removable bioprosthetic heart valve assembly comprising: a bioprosthetic valve configured for coupling to the abutment ring; and, a holder detachably coupled to the bioprosthetic valve, the holder having: a first surface and a second axis perpendicular to the first surface; and a maneuvering system for aligning the first axis and the second axis, the maneuvering system including: a central pin pivotable relative to the holder and rotatable with the holder, wherein the second axis is orthogonal to the central pin; and, a first threadable arcuate bore and a second threadable arcuate bore, each bore having first and second openings disposed at the first surface and first and second threads therethrough, for tilting the first surface and aligning the first axis and the second axis.

Example 29 is a multiple component heart valve prosthesis according to Example 28, further comprising a detachable fit joint having a proximal end and a distal end, the proximal end configured for coupling to the holder and the distal end configured for coupling to an elongated handle.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 8A is a perspective view illustrating a multiple component heart valve prosthesis including an implantation accessory having a fit joint and a holder according to the mechanical heart valve assembly of FIG. 7.

FIG. 8B is an exploded view illustrating the implantation accessory as in FIG. 8A having a holder central pin and attachable to a fit joint.

FIG. 9A illustrates using a sizer in an implantation procedure, according to some embodiments described in the disclosure.

Figure 1:
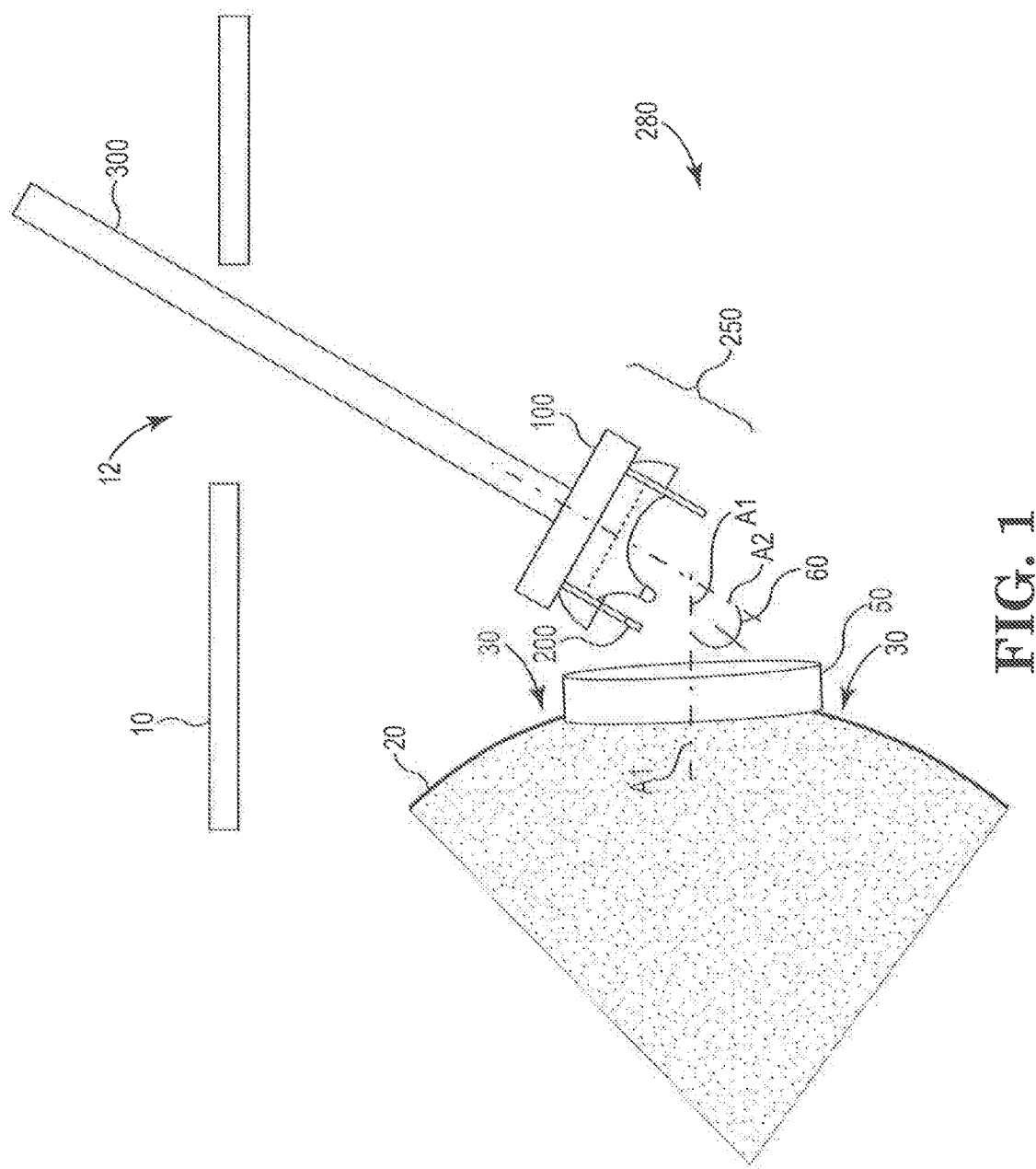
FIG. 1 is a schematic view illustrating a removable bioprosthetic heart valve assembly and implantation into a patient, according to some embodiments described in the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The present device and method can be utilized to improve implantation procedures and performance of heart valve prostheses in a wide variety of applications where the heart valve prosthesis is surgically attached to a prepared valvular rim (or annulus). The embodiments disclosed herein are directed to improved removable bioprosthetic heart valves for implantation into an implantable abutment ring, the removable bioprosthetic heart valve comprising a valve frame having tissue leaflets attached thereto (or alternatively, a mechanical pivotal disk or mechanical leaflets or equivalents thereof). The various aspects of the present invention may be utilized in mitral valve (or other heart valve—aortic, etc.) replacement wherein a prosthetic heart valve frame operates in accordance with a suture ring.

FIG. 1 a schematic view illustrating a removable bioprosthetic heart valve assembly 250 and implantation into a patient, according to some embodiments described in the disclosure. In various embodiments, the removable prosthetic heart valve assembly 250 is a bioprosthetic (i.e., tissue) heart valve assembly. As discussed above, tissue valves generally include a plurality of tissue cusps or leaflets, e.g., made from bovine pericardium or harvested porcine heart valve tissue, mounted onto a stationary metal or plastic frame structure. This frame structure operates to maintain the various cusps or leaflets in a desired orientation and shape that promotes sufficient valve opening and closing characteristics and proper blood flow.

In various other embodiments, the prosthetic heart valve assembly 250 is a mechanical heart valve assembly. As mentioned above, a modern mechanical heart valve prosthesis is typically formed of an annular valve seat in a relatively rigid valve body and includes an occluding disk or pair of leaflets that moves between a closed, seated position and an open position in a prescribed range of motion.

While the embodiments discussed herein can operate to employ either bioprosthetic or mechanical heart valves, the discussion below is provided with reference to bioprosthetic heart valves as shown in FIGS. 1-6. It should be appreciated, however, that mechanical heart valves (as shown in FIGS. 7 and 8) may also be employed with the embodiments discussed herein, and that reference to bioprosthetic heart valves should not serve to limit the scope of this disclosure.

In one embodiment, removable bioprosthetic heart valve assembly 250 for implantation into an implantable abutment ring 50 includes valve frame 200 having tissue leaflets therein and holder 100. As discussed in greater detail below, abutment ring 50 is configured to receive valve frame 200, and valve frame 200 is configured to be received by abutment ring 50. Together, holder 100, valve frame 200, and a plurality of tissue leaflets (not shown) located within the valve frame 200 generally make up the structure of the removable bioprosthetic heart valve assembly 250. Together, removable bioprosthetic heart valve assembly 250 and abutment ring 50 generally make a multiple component heart valve prosthesis 280 for implantation at a heart valve annulus location of a patient's heart, in its assembled configuration. As mentioned, removable bioprosthetic heart valve assembly 250 includes holder 100 for maneuvering and implanting valve frame 200 into abutment ring 50. Advantageously, holder 100 is detachable and removable after successful implantation of valve frame 200 into abutment ring 50. Valve frame 200 is interchangeably referred to herein as valve 200, and it is understood that valve or valve frame 200 further includes a plurality of tissue leaflets located within the valve frame 200.

As shown in FIG. 1, removable bioprosthetic heart valve assembly 250 for implantation into abutment ring 50, having axis A1, is attached at heart valve annulus location 30 of a patient's heart. Patient 10, in a minimally-invasive access approach, for example, is entered through patient chest opening 12 to access ventricle 20. Abutment ring 50 is secured to patient annulus 30. Abutment ring 50 includes axis A1 passing through its center. Axis A1 is generally perpendicular to the annulus. Once secured to annulus 30, there is limited access to abutment ring 50 due to physical constraints within patient 10, thus making implantation of valve 200 challenging.

Removable bioprosthetic heart valve assembly 250 comprises bioprosthetic valve 200 for coupling to abutment ring 50, and holder 100 detachably coupled to valve 200. To facilitate implanting valve 200, holder 100 is coupled also to handle 300 via fit joint (160, shown in FIG. 2B). Holder 100, coupled to valve 200, includes surface 110 and axis A2. Axis A2 is perpendicular to surface 110. Surface 110 is planar and disc shaped to couple with valve 200. Upon inserting holder 100 via handle 300 through opening 12, axis A2 is offset to axis A1 by angle 60. Angle 60 is an acute angle, ranging in measurement from less than 90 degrees but more than zero degrees. Holder 100 further includes maneuvering system 120 (FIG. 3) for aligning axis A2 with axis A1. Alignment of axes A1 and A2 prior to seating of valve 200 into abutment ring 50 ensures proper implantation of valve 200 into abutment ring 50. Holder 100, having maneuvering system 120, is interchangeably referred to herein as tiltable holder 100. In some embodiments, abutment ring 50 is attachable to a patient's mitral valve rim.

Figure 2B:
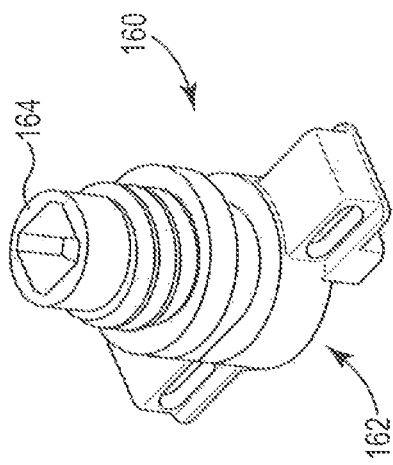
FIG. 2B is a perspective view illustrating a fit joint of the removable bioprosthetic heart valve assembly of FIG. 2A.
Figure 2C:
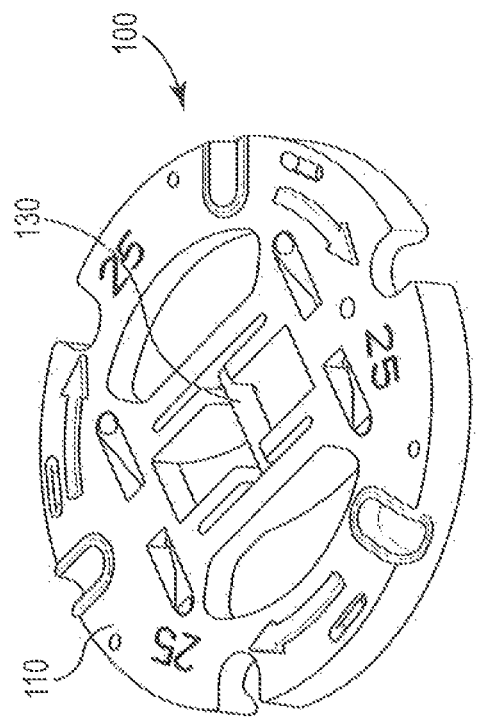
FIG. 2C is a perspective view illustrating a holder template of the removable bioprosthetic heart valve assembly of FIG. 2A.
Figure 2A:
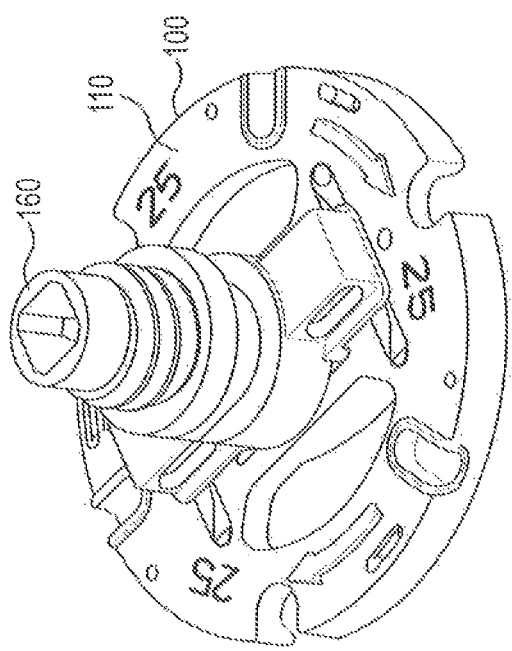
FIG. 2A is a perspective view illustrating a holder comprising a fit joint and a holder template of the removable bioprosthetic heart valve assembly of FIG. 1.

FIG. 2A is a perspective view illustrating holder 100 and fit joint 160 for removable bioprosthetic heart valve assembly 250 as shown in FIG. 1. Holder 100 is coupled to fit joint 160. FIG. 2B is a perspective view illustrating fit joint 160 as in FIG. 2A. Fit joint 160 includes proximal end 162 and distal end 164, proximal end 162 is configured for coupling to holder 100 and distal end 164 is configured for coupling to elongated handle 300 (as shown in FIG. 1). Fit joint 160 is detachable as needed. Advantageously, fit joint 160 detaches from holder 100 to allow access to maneuvering system 120 by the physician using, for example, MICS forceps. FIG. 2C is a perspective view illustrating holder 100 for detachable coupling to fit joint 160 as in FIG. 2B. Holder 100 is interchangeably referred to herein as holder template.

Figure 3:
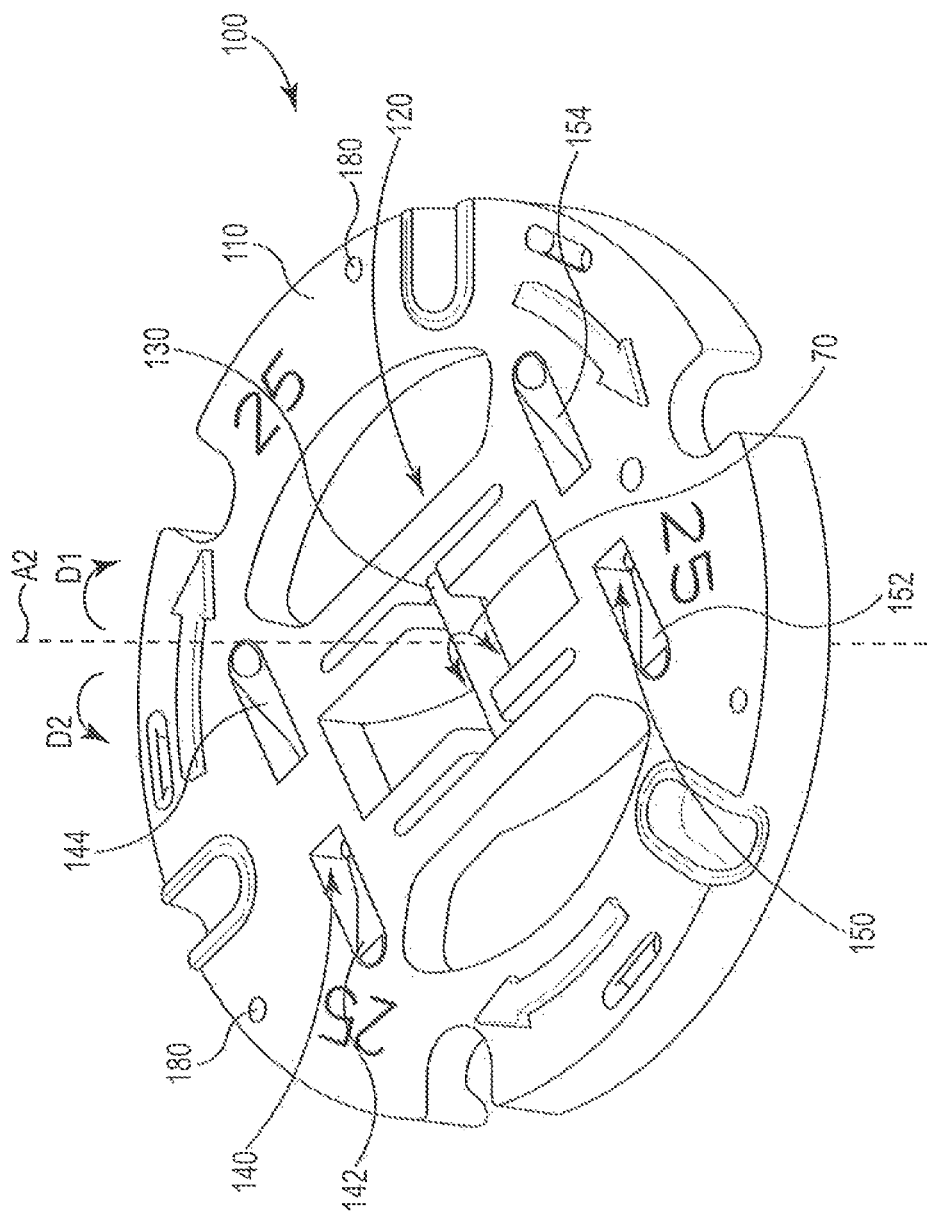
FIG. 3 is a perspective view illustrating a holder template of the removable bioprosthetic heart valve assembly of FIG. 1.

FIG. 3 is a perspective view illustrating holder 100 of removable bioprosthetic heart valve assembly 250. Holder 100, having axis A2, includes surface 110 and maneuvering system 120. Maneuvering system 120 includes central pin 130 pivotable relative to holder 100, pivoting as indicated by direction 70. Axis A2 passes through central pin 130. Central pin 130 is further rotatable with the holder in a first clockwise direction D1 and in a second counter-clockwise direction D2. In some embodiments, central pin 130 is attachable to a minimally invasive cardiothoracic surgery (MICS) forceps for ease in maneuverability. Maneuvering system 120 further includes threadable arcuate bores 140 and 150. Each threadable arcuate bore, bores 140 and 150, include first and second openings disposed at surface 110. Bore 140 includes openings 142 and 144. Bore 150 includes openings 152 and 154.

Figure 4:
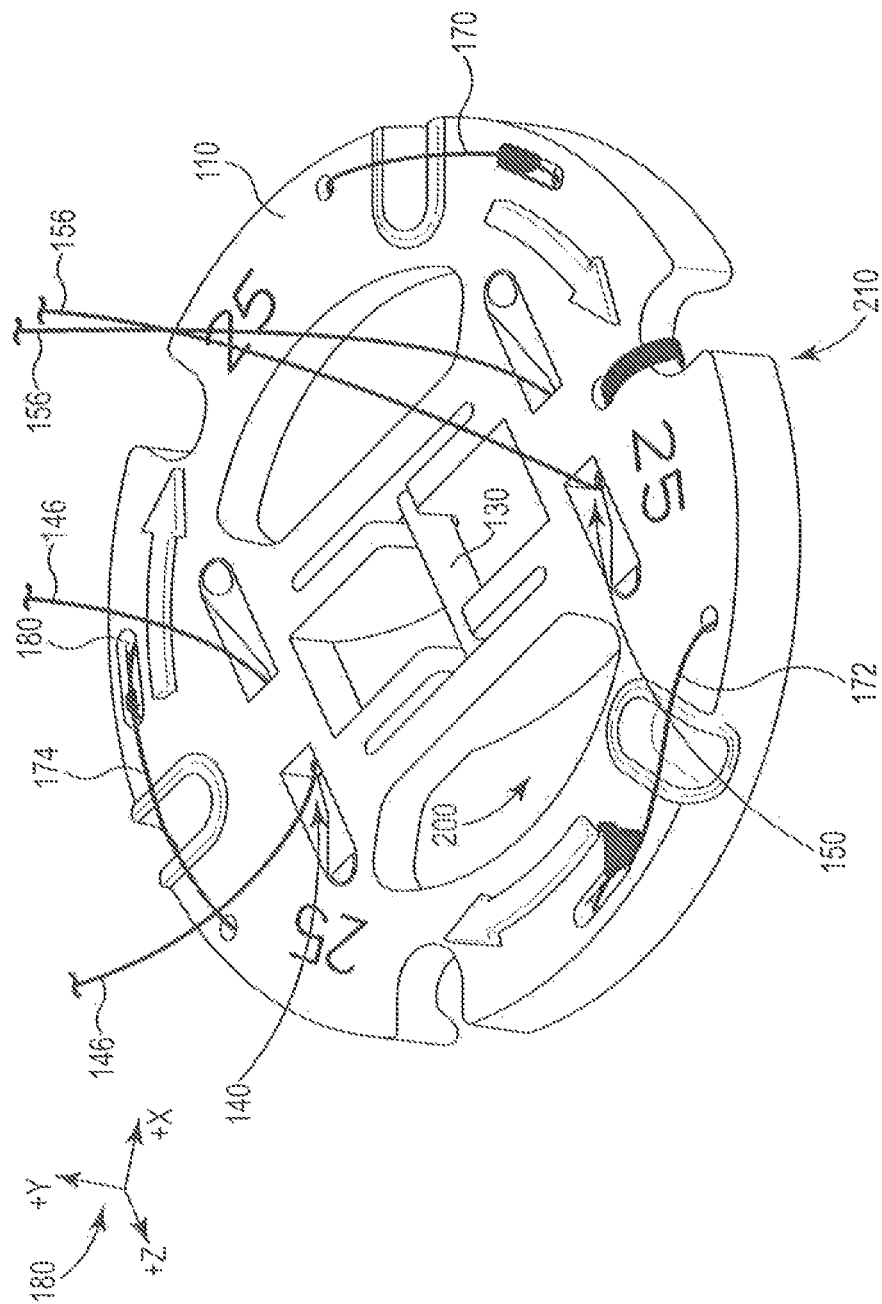
FIG. 4 is a perspective view illustrating a holder template having a retaining system to affix to a valve, and a maneuvering system for tilting, of the removable bioprosthetic heart valve assembly of FIG. 1.

FIG. 4 is a perspective view illustrating holder 100 of removable bioprosthetic heart valve assembly 250. Threadable arcuate bore 140 and threadable arcuate bore 150 include threads 146 and 156 therethrough, respectively. Manipulation or pulling on threads 146 and 156, while grasping the central pin 130 (e.g., with a MICS forceps), operate to tilt surface 110 and aligning axis A1 and axis A2. Surface 110 is tiltable about axis z (see coordinates 180), which extends parallel to the central pin 130. Advantageously, surface 110 is maneuverable to align axes A1 and A2 when holder 100 and valve 200, as coupled, are proximate abutment ring 50. In some embodiments, a retaining surgical suture may be attached to at least one of the bores 140, 150. This retaining suture may extend to outside the patient (e.g., to the surgeon) and may be used to ensure the device does not get lost inside the patient.

FIG. 4 also illustrates holes 180 through the thickness of holder 100, the holes extending from surface 110 to surface 210 opposite thereof. These holes enable coupling of holder 100 to valve 200 and include sutures 170, 172, and 174 for attachment as shown in FIG. 4. Advantageously, sutures 170, 172, and 174 can be cut after successful seating and securing of valve 200 into abutment ring 50. Thusly, holder 100 is detachable and able to be removed from the patient. Holders 100 are sized according to patient valve requirements and are generally formed of a biocompatible metal (e.g., titanium, stainless steel, or other suitable metal alloy), a plastic material (e.g., acetal homopolymer plastic) or of any other suitable biocompatible material. Holder 100 is detachable and disposable, suitable for single-use.

Figure 5B:
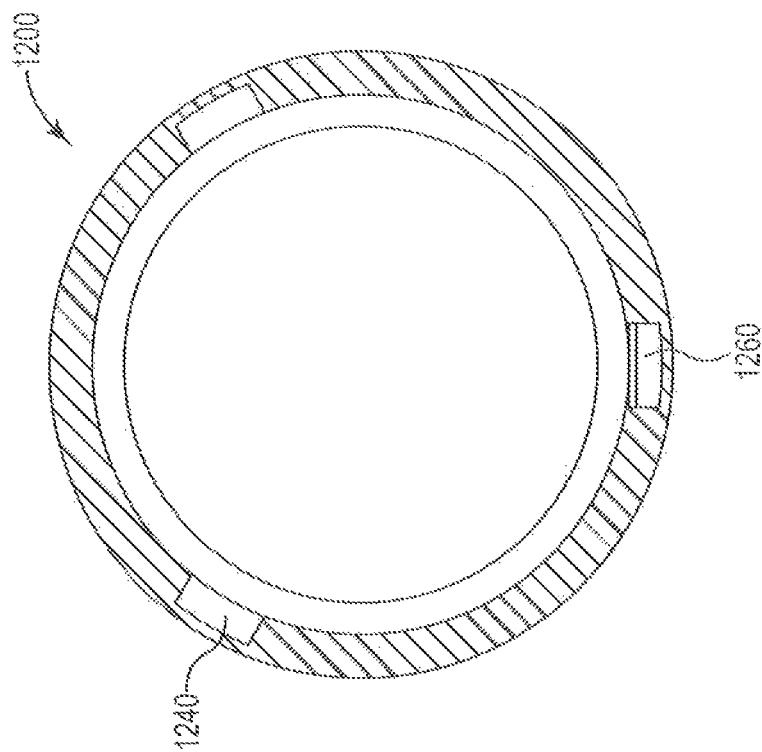
FIG. 5B is a top view of the removable bioprosthetic heart valve assembly of FIG. 5A, in an engaged configuration.
Figure 5A:
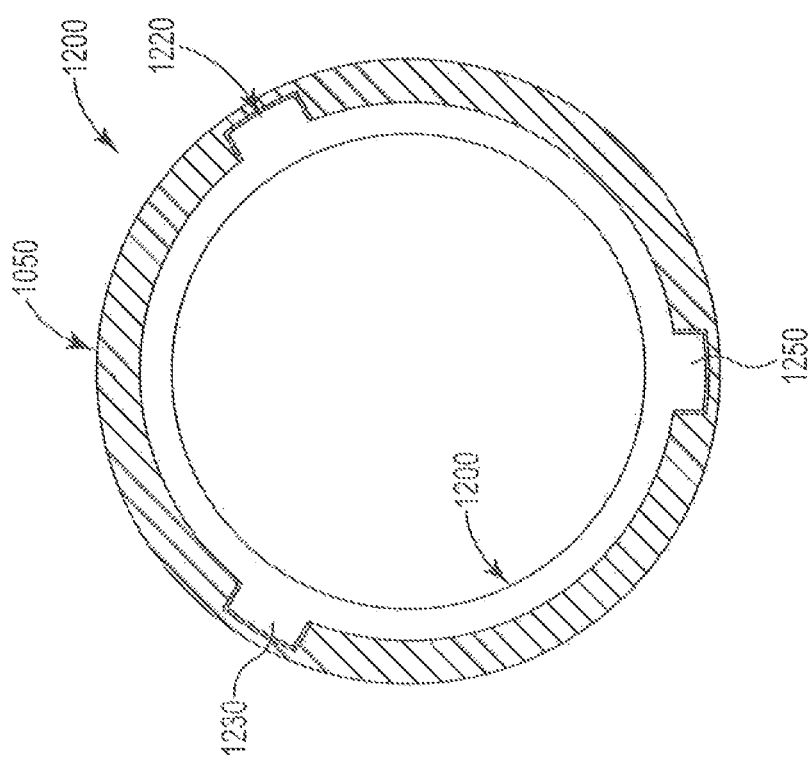
FIG. 5A is a top view of the removable bioprosthetic heart valve assembly of FIG. 1, in a disengaged configuration.

FIGS. 5A and 5B are top-views of removable bioprosthetic heart valve assembly 250 according to some embodiments. In some embodiments, heart valve assembly 250 includes a two-piece mechanical heart valve. FIG. 5A illustrates abutment ring 1050 and valve frame 1200 in a disengaged configuration 1250. Abutment ring 1050 includes locking system 1220. In some embodiments, locking system 1220 includes one or more notches capable of accepting locking features on valve frame 1200, along with a channel extending between the notches to allow rotation of the locking features through the channel to a position not aligned with the notches in the locking system to an engaged position (also referred to herein as a "locked" position). Valve frame 1200 includes at least one locking feature 1230. As shown in FIG. 5A, the valve frame 1200 includes three locking features, which protrude radially outward to mate with the valve system 1220.

FIG. 5B illustrates abutment ring 1050 and valve frame 1200 in an engaged configuration 1260. The at least one locking feature 1230 is configured to be received by the locking system, for example by channel 1240 of abutment ring 1050 extending between the notches. International Application No. PCT/IB2016/053515, which is incorporated by reference herein, describes locking systems suitable in removable bioprosthetic valve assemblies according to at least some embodiments of the present disclosure. When the locking features of the valve frame 1200 are mated with the notches of the locking system 1220, the maneuvering system having central pin (130 as shown in FIG. 4) may be used to rotate the valve frame 1200 relative to the abutment ring 1050 in a first (e.g., clockwise) direction into the locked position. Likewise, the maneuvering system may be used to rotate the valve from 1200 relative to the abutment ring 1050 in a second (e.g., counter-clockwise) direction to a disengaged position. This enables the valve to be seated and secured to the abutment ring after alignment of axes A1 and A2. Likewise, it conversely allows the valve to be disengaged and removed from the abutment ring.

Generally in some embodiments of the present disclosure, and in advance of inserting a holder/valve assembly, an implantation accessory such as a sizer is introduced into the native valve annulus in order to evaluate the size of the annulus. In some embodiments, multiple sizers having different dimensions are introduced independently for annulus size determination. For example, the medical team may have three or four sizers of varying dimensions available to perform the sizing procedure with sizer 500. That way, an appropriate sized corresponding holder/valve assembly can be selected by the medical team that best fits the native valve annulus, thus ensuring a successful procedure, which include (among others) implantation of a bioprosthetic heart valve, a mechanical heart valve and an annuloplasty ring.

Figure 6:
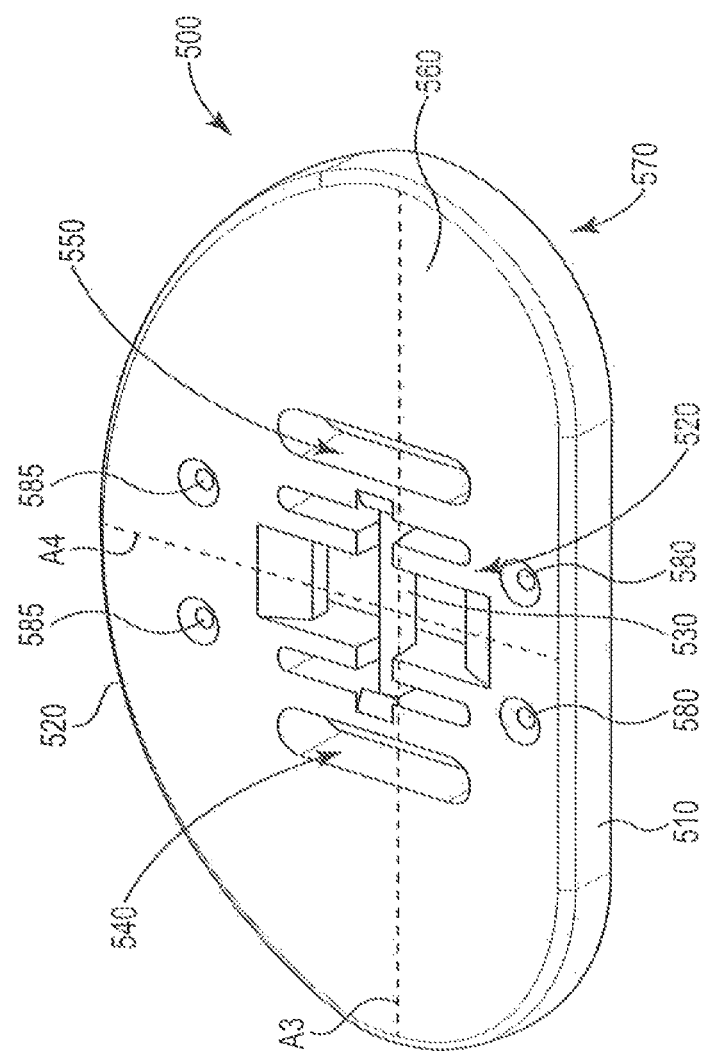
FIG. 6 is a perspective view illustrating a sizer according to other embodiments described in the disclosure.
Figure 7:
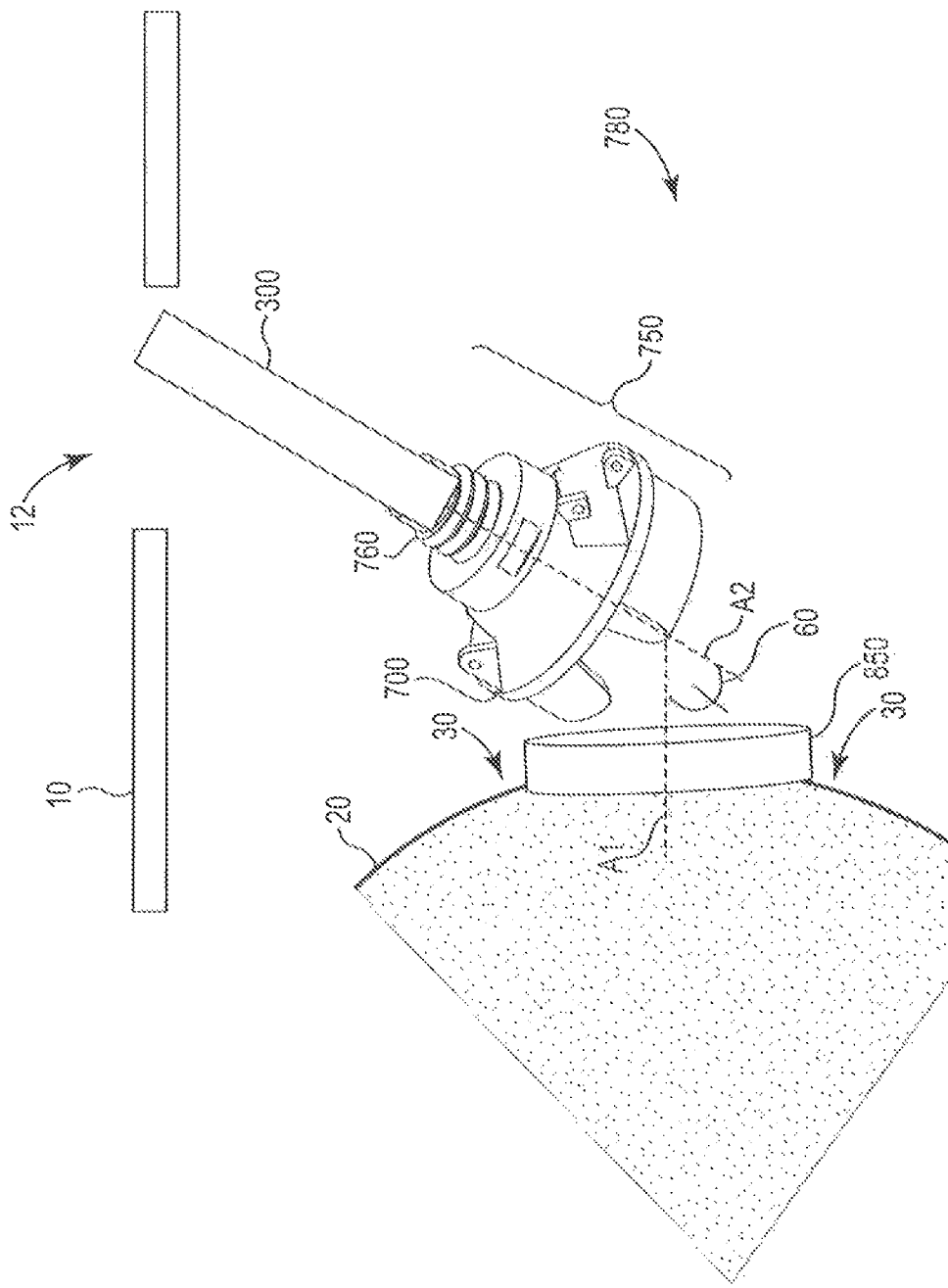
FIG. 7 is a schematic view illustrating a mechanical heart valve assembly and implantation into a patient, according to some embodiments described in the disclosure.

FIG. 6 is a perspective view illustrating a sizer 500 for determining annulus size. Sizer 500, which may also be referred to interchangeably herein as D-shaped sizer 500, is designed to complement a D-shaped mitral annulus, for example. D-shaped refers to an approximate shape including a long side 510 and a curved profile side 520. Side 510 is generally placed anteriorly in the patient, while side 520 is generally placed posteriorly. Sizer 500 includes a long axis A3 and a short axis A4 as shown on FIG. 6. According to various embodiments, long axis A3 of sizer 500 ranges from 24 mm to 42 mm. According to some embodiments, the long axis A3 is 24 mm, or 26 mm, or 28 mm, or 30 mm, or 32 mm, or 34 mm, or 36 mm, or 38 mm, or 40 mm, or 42 mm. According to exemplary embodiments, the ratio of the long axis to the short axis A3/A4 ranges from 1.3 to 1.5. Advantageously, sizer 500 for use with mitral valve prosthesis and annuloplasty rings provides for minimally invasive procedures with a reduced height for insertion through a small wound, as for example in a MICS procedure. In other words, sizer 500 is shaped such that it corresponds to the shape of the native valve annulus, while also having a thickness capable of insertion through a space between the ribs of the patient during the procedure.

As shown in FIG. 6, sizer 500 includes central pin 530 for grasping and maneuvering with a MICS forceps. FIG. 6 also illustrates holes 580 and 585 through the thickness of sizer 500, the holes extending from surface 560 to surface 570 opposite thereof. Threadable holes 580 and 585 are for inserting threads therethrough (i.e. one thread through holes 580 and a second thread through holes 585). Threads passing through holes or openings 580 and 585 can also be used for maneuvering the sizer, i.e. tipping or angling surface 560, by pulling or maneuvering the threads in similar manner as for threadable arcuate bores 140 and 150 for holder 100 of FIG. 4. As noted above, in various embodiments, the threads are also used to help ensure the sizer 500 is not left behind in the patient. In some embodiments, holes 580 is referred to interchangeably herein as a first threadable bore formed by the pair of holes 580; and holes 585 is referred to interchangeably herein as a second threadable bore formed by the pair of holes 585. Maneuvering system 520, including central pin 530 and threadable holes 580 and 585, operates similarly as described for system 120 for holder 100. Sizer 500 further includes bores or slots 540 and 550, slots 540 and 550 configured to allow coupling of the central fit joint to the sizes 500, in a manner as described similarly as shown for fit joint 160 of FIG. 2B. This allows the connection of a handle to parachute the sizers to the annulus. Such parachuting may also be accomplished using a MICS forceps to engage the central pin 530. Surface 570 of sizer 500 is placed adjacent to and/or in contact with the patient's annulus during sizing, while surface 560 faces the direction of the physician performing the sizing. For a MICS procedure, the fit joint may be removed to allow the sizer to be tilted for insertion through a small incision.

Generally in some embodiments of the present disclosure, an implantation accessory for placement at a patient's heart valve annulus location is provided. In some embodiments, the accessory includes a mechanical heart valve for placement at a patient's native valve annulus. The native valve annulus can be at an aortic valve or at a mitral valve location. In some embodiments, the implantation accessory includes a rotator to rotate the already implanted valve in order to orient or reposition the leaflet(s) of the mechanical heart valve. In FIG. 7, implantation accessory 700 is shown for implantation into mechanical heart valve 850, which includes valve housing attached at heart valve annulus location 30 of a patient's heart. Valve 850 is also referred to as valve housing 850 interchangeably herein. Implantation accessory 700 is also referred to interchangeably herein as rotator 700 or as holder 700. Using rotator 700, the valve 850 rotates within its housing for fine tuning and leaflet orientation after valve implantation. Implantation assembly 650 includes mechanical heart valve 850 (see FIGS. 8A and 8F) and rotator 700. Valve 850 further includes leaflets 860. Multiple component heart valve accessory 780 includes rotator 700 and fit joint 760, which may be similar to the above-described fit joint 160. Fit joint 760 is attachable to handle 300. Patient 10, in a minimally-invasive access approach, for example, is entered through patient chest opening 12 to access ventricle 20. Mechanical heart valve 850 is secured to patient annulus 30 and includes axis A1 passing through its center as shown in FIG. 7. Axis A1 is generally perpendicular to the annulus. Once secured to annulus 30, there is limited access to valve 850 due to physical constraints within patient 10, thus making positioning of mechanical heart valve 850 and orientation of leaflets 860 challenging.

Figure 8D:
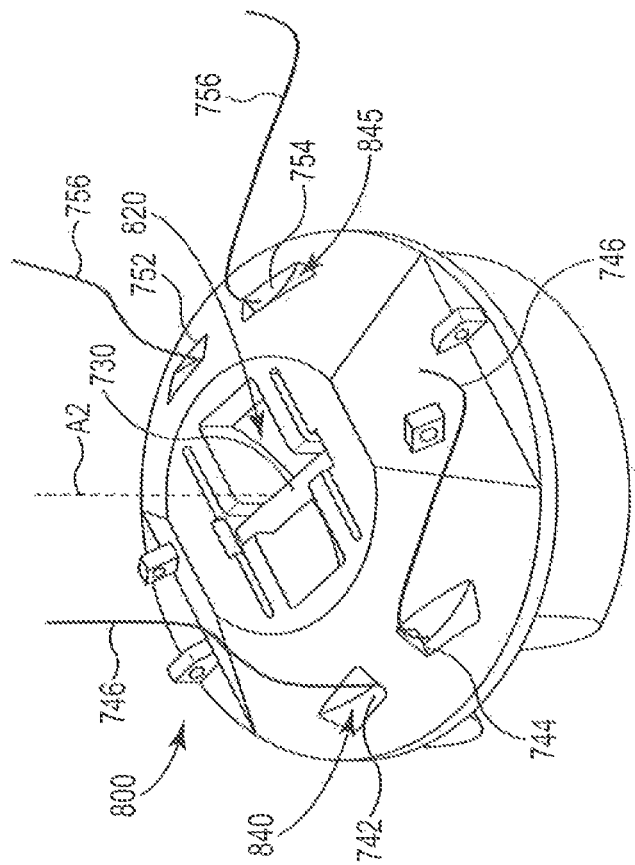
FIG. 8D is a perspective view of another embodiment of the holder of an implantation accessory illustrating the maneuvering system including threadable bores according to some embodiments described in the disclosure.

As shown in FIGS. 8A-8F, implantation assembly 650 comprises mechanical valve 650 (coupled with valve housing 850) and rotator 700 detachably coupled to valve 850. To facilitate implanting valve 850, rotator 700 is coupled also to handle 300 via fit joint 760 as shown in FIG. 8A. Fit joint 760 and rotator 700 are two separate components shown coupled together in FIG. 8A. Rotator 700 is further useful in rotating or aligning leaflets 860 within valve housing 850 by using maneuvering system 720. Implantation accessory 780, as shown in the exploded view of FIG. 8B, includes rotator 700 having central pin 730, the rotator 700 attachable to fit joint 760. Component 700, which is a rotator or holder, includes central pin 730. Fit joint 760 is useful for valve placement by a physician when an open chest is accessible wherein holder 780 is used assembled. In a minimally invasive procedure, the fit joint 760 is removed outside of the patient before insertion of the assembly so that only the rotator 700 remains on the valve, thereby reducing the height of the implantation accessory and allowing insertion through a small wound. In the embodiments disclosed herein, fit joint 760 is removed prior to implantation and, therefore, the maneuvering system 720 is fully exposed and accessible to be used by the physician in a similar manner as for maneuvering system 120 as detailed above. Central pin 730 operates similarly as described for central pin 130 for holder 100 and is graspable by forceps. Rotator 700 includes holes 770 and 775. Holes 770 and 775 allow fixing the valve 850 to holder 700 by threading threads therethrough and is also referred to as a retaining system to affix to a valve. Teeth 758 of fit joint 760 facilitate coupling to rotator 700 via a snap fit connection wherein teeth 758 mate with holes 745 of holder 700. After the valve 850 has been detached from rotator 700, both holes 770 are used to insert the surgical thread by the physician to tilt the holder as part of maneuvering system 720 working in conjunction with forceps grasping the rotatable central pin 730.

Figure 8F:
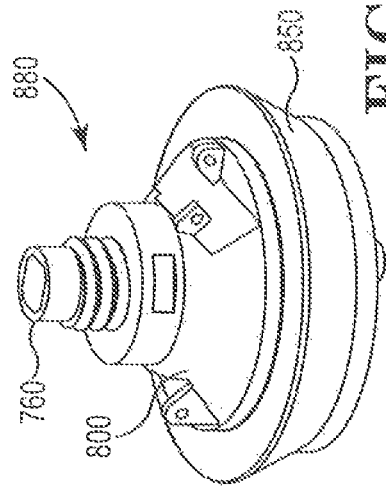
FIG. 8F is a perspective view illustrating the multiple component heart valve prosthesis of FIG. 8A coupled with the implantation accessory according to some embodiments described in the disclosure.
Figure 8C:
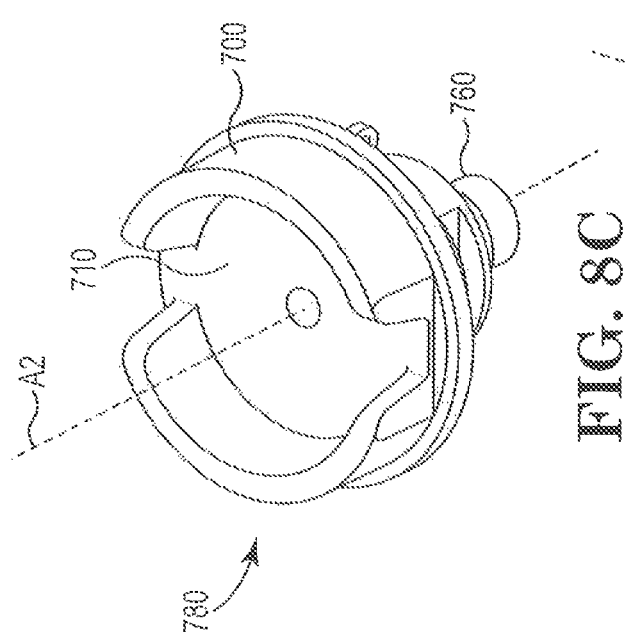
FIG. 8C is a perspective view illustrating an alternate view of the implantation accessory of FIGS. 8A and 8B, the underside having a planar surface perpendicular to axis A2.

As shown in FIG. 8C, rotator 700 includes surface 710 and axis A2. Axis A2 is perpendicular to surface 710. Surface 710 is planar and disk shaped to couple with valve 850. Upon inserting rotator 700 via handle 300 through opening 12 as shown in FIG. 7, axis A2 is offset to axis A1 by at an acute angle, angle 60, ranging in measurement from less than 90 degrees but more than zero degrees.

An alternate embodiment of an implantation accessory or rotator is shown as in FIG. 8D. Rotator 800 is similar to rotator 700 of FIG. 8B except that rotator 800 having maneuvering system 820 includes threadable arcuate bores 840 and 845, the bores being threadable for tilting the rotator similarly as for arcuate bores 140 and 150 for holder 100 as detailed above and as shown in FIG. 4. Rotator 800 includes maneuvering system 820 for aligning axis A2 with axis A1, maneuvering system 820 including central pin 730. Alignment of axes A1 and A2 prior to seating of valve 850 ensures proper implantation of valve 850 and orientation of valve leaflets 860, which may be metallic, into valve housing 850. Implantation accessory 800 is configured to position a plurality of leaflets 860 of the removable mechanical heart valve assembly 850. Positioning leaflets includes at least one of pivoting and tilting. Rotator 800 is interchangeably referred to herein as tiltable rotator 800. In some embodiments, valve housing 850 is attachable to a patient's mitral valve rim via a sewing cuff. In other embodiments, valve housing 850 is attachable to a patient's aortic valve rim.

Figure 8E:
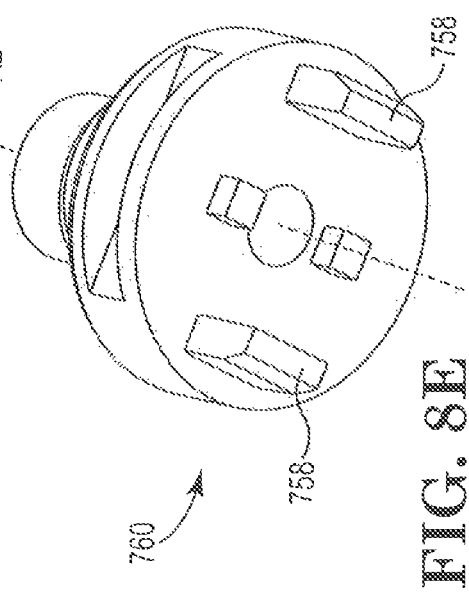
FIG. 8E is a perspective view illustrating the attachment means of the fit joint as in FIG. 8B.

In some embodiments, central pin 730 is attachable to a minimally invasive cardiothoracic surgery (MICS) forceps. As shown in FIG. 8D, rotator 800 includes central pin 730 for grasping and maneuvering with a MICS forceps. While grasping central pin 730 with minimally invasive cardiothoracic surgery (MICS) forceps is not shown in FIGS. 8A-8F, central pin 730 is graspable by MICS forceps similarly as shown for the embodiment having central pin 520 as in FIG. 9A or as in the embodiment having central pin 130 as in FIGS. 9E and 9F. Maneuvering system 820, including central pin 730 and threadable bores 840 and 845, operates similarly as described for system 120 for holder 100. Central pin 730 is pivotable relative to surface 710, and the second axis A2 passes through and is orthogonal to the central pin 730. Threadable bore 840 includes openings 742 and 744, and threadable bore 845 includes openings 752 and 754, the bores and openings for receiving first and second threads 746 and 756 therethrough, respectively, for tilting the surface 710 and aligning the first axis A1 and the second axis A2. As shown in FIG. 8E, fit joint 760 includes snap fit prongs or teeth 758 for attachment to rotator 700. FIG. 8F illustrates schematically the multiple component heart valve prosthesis 880 positioned into valve housing 850.

More generally in some embodiments of the present disclosure, an implantation accessory for placement at a heart valve annulus location of a patient's heart is provided. The annulus has a first axis (refer to A1 of FIG. 9A). The implantation accessory (100, 500, 700, 800) comprises a first surface (i.e. 110 of FIGS. 3 and 4, or 560 of FIG. 9A, or 710 of FIG. 8A) having a second axis perpendicular to the first surface. The implantation accessory (100, 500, 700, 800) includes a maneuvering system (120, 520, 720, 820) for aligning the first axis and the second axis. The maneuvering system (120, 520, 720, 820) includes a central pin (130, 530, 730) pivotable relative to the surface (110, 560, 710). The second axis passes through the central pin. The maneuvering system (120, 520, 720, 820) includes a first threadable bore (140, 580, 740) and a second threadable bore (150, 585, 750), each bore having first and second openings disposed at the first surface. The first threadable bore and the second threadable bore include a first thread and a second thread therethrough, respectively, for tilting the first surface and aligning the first axis and the second axis. The central pin (130, 530, 730) is attachable to a minimally invasive cardiothoracic surgery (MICS) forceps (2500 of FIGS. 9A and 9F). In some embodiments, the implantation accessory is configured to size the annulus and the implantation accessory is referred to as a sizer. In other embodiments, the implantation accessory is configured to implant a removable bioprosthetic heart valve assembly and the implantation accessory is referred to as a holder or template. In yet other embodiments, the implantation accessory is configured to implant a removable mechanical heart valve assembly and the implantation accessory is referred to as a rotator.

Figure 9B:
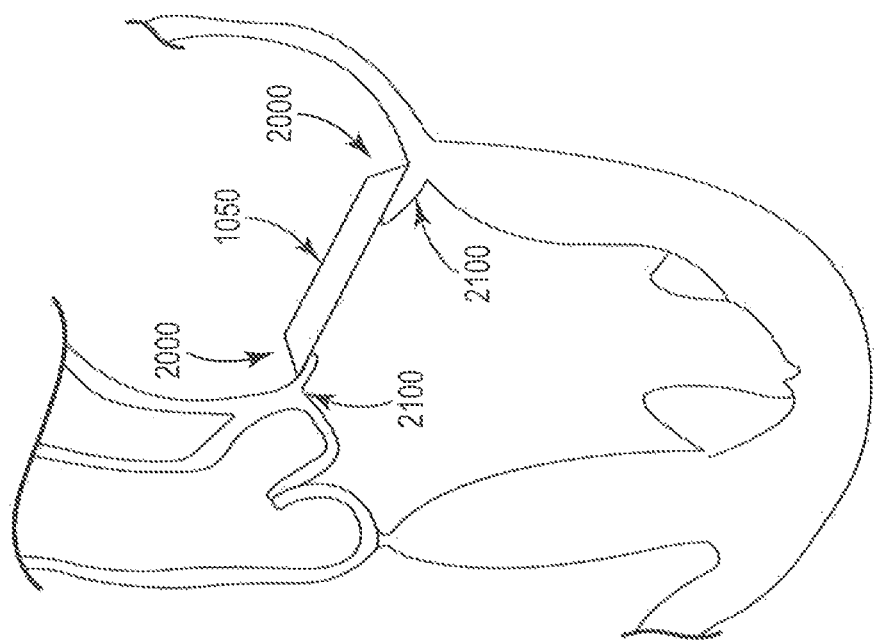
FIG. 9B illustrates insertion of an abutment ring according to an implantation procedure of the removable bioprosthetic heart valve assembly, according to some embodiments described in the disclosure.

FIGS. 9A to 9F illustrate a method for implanting a multiple component heart valve prosthesis 280, according to some embodiments described in the disclosure. The method optionally includes sizing the native annulus as shown in FIG. 9A. Sizer 500 is advanced near annulus 2100 of a patient. Sizer 500 is attachable or graspable to MICS forceps 2500 to facilitate advancement and placement of sizer 500 close to annulus. Sizer 500 is maneuverable by grasping central pin 530 and/or adjusting thread 545 or 556 to angle surface 560 as needed to position sizer 500 into annulus 2100. Sizer 500, including axis A2 perpendicular to surface 560, is maneuverable to align axis A1 corresponding to the central axis of the annulus with axis A2. Sizing is repeated as needed with different dimension sizers 500 until an appropriate fit of the sizer to the annulus is achieved by the user. Thereby, the appropriate sized removable bioprosthetic heart valve assembly 1300 is selected. While the sizer 500 in FIG. 9A is shown having an approximate D-shape cross-section, in other embodiments, the sizer 500 is substantially circular in cross-section, similar to the cross sectional shape of the typical prosthetic valve.

Figure 9C:
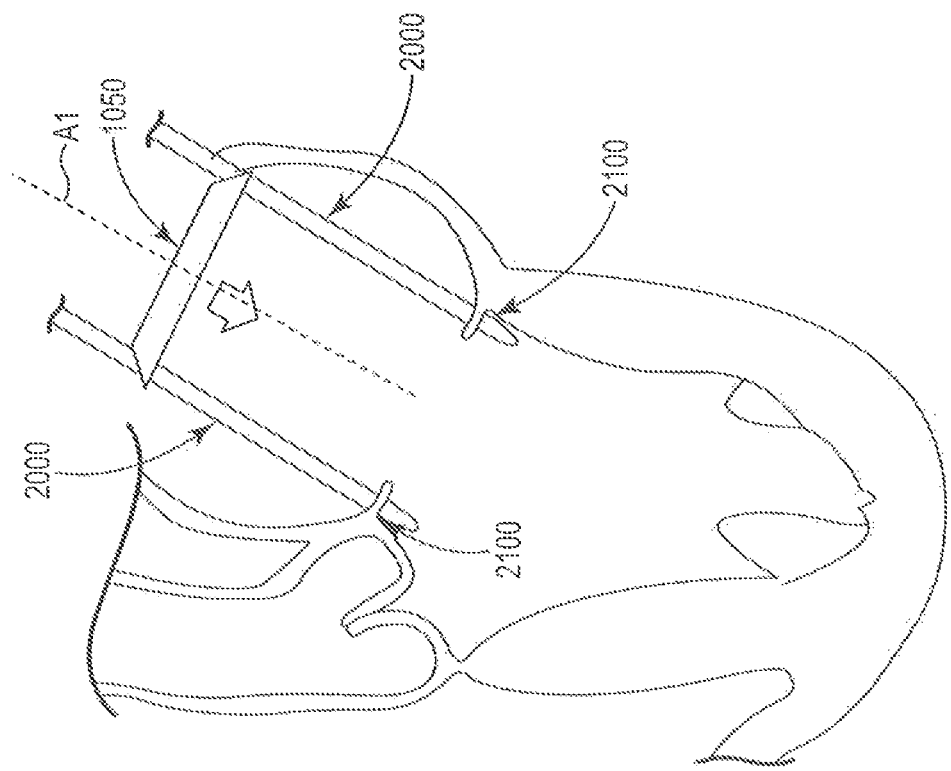
FIG. 9C illustrates securement of an abutment ring according to an implantation procedure of the removable bioprosthetic heart valve assembly, according to some embodiments described in the disclosure.

The method includes, as shown in FIGS. 9B and 9C, inserting and securing abutment ring 1050 to heart valve annulus 2100 of a patient's heart via sutures 2000. Abutment ring 1050 has a first axis A1. The method further includes, as shown in FIG. 9D, advancing removable bioprosthetic heart valve assembly 1300 to abutment ring 1050. As assembly 1300 is advanced, axes A1 and A2 are not aligned (see FIG. 9D) due to physical constraints upon entering the patient. Removable bioprosthetic heart valve assembly 1300 comprises bioprosthetic valve 1320 for coupling to abutment ring 1050 and holder 1310 detachably coupled to bioprosthetic valve 1320. In some embodiments, the method includes wherein the removable bioprosthetic heart valve assembly further comprises a detachable fit joint having a proximal end and a distal end, the proximal end coupled to the holder and the distal end coupled to an elongated handle, and wherein the step of advancing further includes inserting the removable bioprosthetic heart valve assembly via the handle (not shown). Referring also to FIGS. 1 and 2, the advancement includes advancing holder 100 attached to fit joint 160 and handle 300; the holder includes a first surface, second axis A2 perpendicular to the first surface, and a maneuvering system for aligning axes A1 and A2 (accessible upon removal of the fit joint 160). In some embodiments, detaching the fit joint coupled to the elongated handle from the valve assembly before advancing the valve into the patient. Maneuvering by pivoting the central pin using an attachable minimally invasive cardiothoracic surgery (MICS) forceps 2500 is shown as in FIGS. 9D and 9E.

Figure 9E:
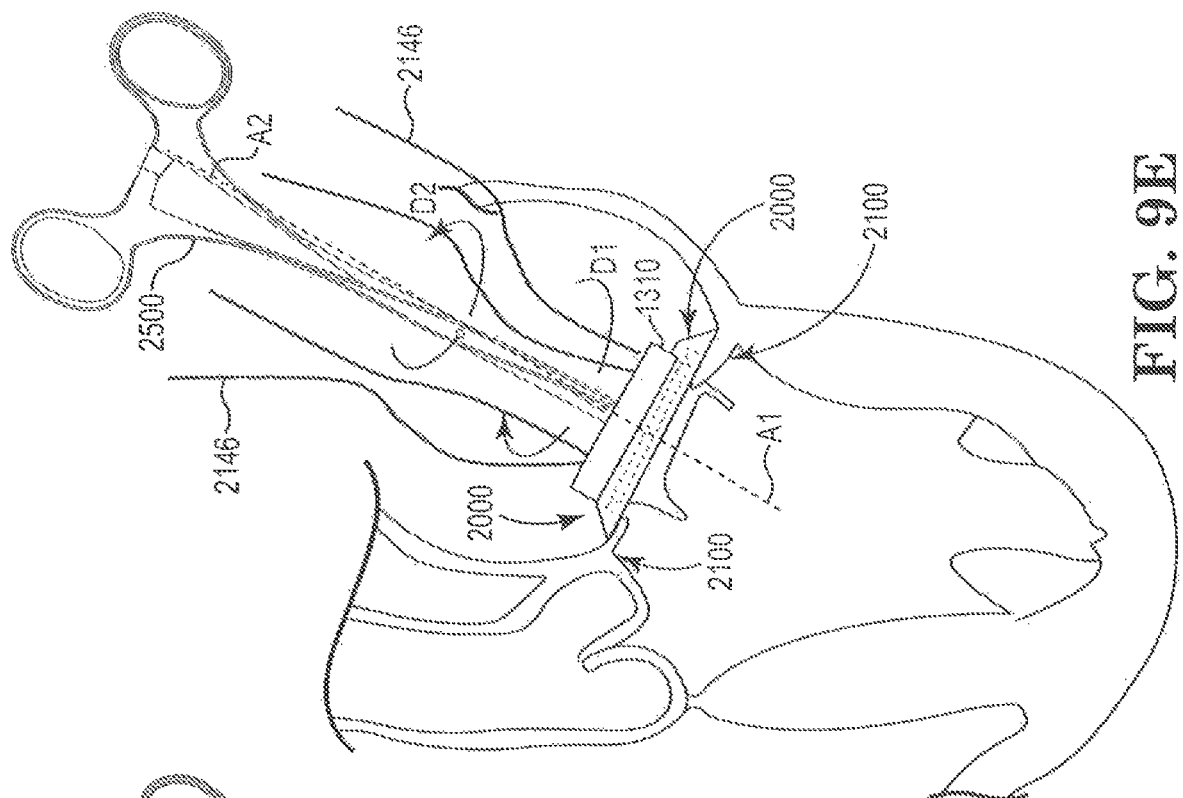
FIG. 9E illustrates maneuvering, alignment and locking of a holder/valve assembly according to an implantation procedure of the removable bioprosthetic heart valve assembly, according to some embodiments described in the disclosure.
Figure 9D:
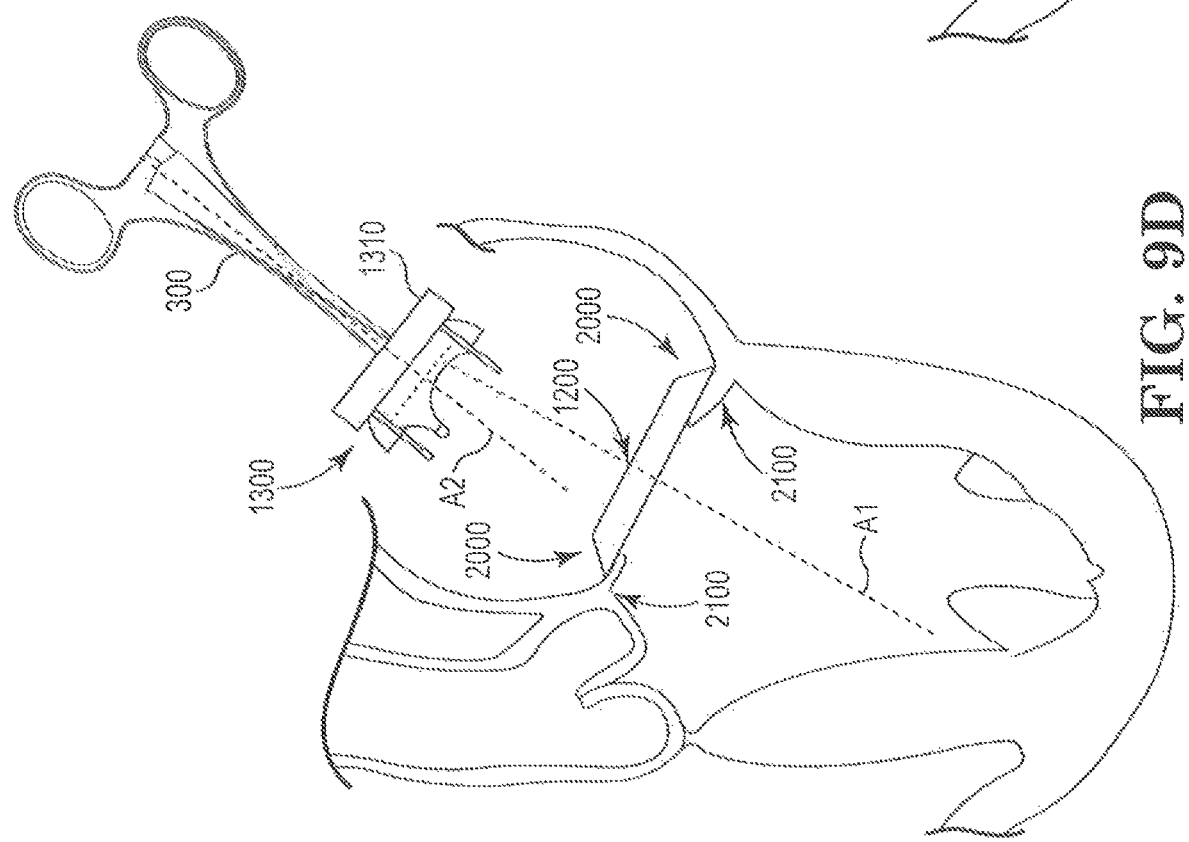
FIG. 9D illustrates advancement of holder/valve assembly according to an implantation procedure of the removable bioprosthetic heart valve assembly, according to some embodiments described in the disclosure.

As shown in FIG. 9E, the method further includes maneuvering the maneuvering system to align axes A1 and A2. Referring also to FIGS. 1 through 4, maneuvering includes pivoting the central pin 130, using for example MICS forceps 2500, and/or by tilting the first surface by manipulating or pulling on threads 2146 and 2156 as shown in FIG. 9E. In some embodiments, the method includes wherein the maneuvering system comprises a central pin pivotable relative to the holder, axis A2 passing through the central pin 130, and wherein the step of maneuvering includes pivoting the central pin using an attachable minimally invasive cardiothoracic surgery (MICS) forceps 2500. In some embodiments, the method includes wherein the central pin is rotatable with the holder, and wherein the step of maneuvering includes rotating the holder in a clockwise direction D1 to engage or lock the valve assembly 1300 with the abutment ring 1050 and in a counter-clockwise direction D2 to disengage the valve assembly from the abutment ring. In some embodiments, the method includes wherein the maneuvering system comprises a first threadable arcuate bore and a second threadable arcuate bore, each bore having first and second openings disposed at the first surface and first and second threads disposed therethrough, and wherein the step of maneuvering includes pulling on the first and second threads (2146, 2156) to tilt the first surface and to align the first axis and the second axis.

Once axes A1 and A2 are aligned, the method further includes seating the bioprosthetic valve by further advancing the removable bioprosthetic heart valve assembly into the abutment ring and coupling the bioprosthetic valve to the abutment ring. In some embodiments, the method includes wherein the abutment ring includes a locking system and the bioprosthetic valve includes at least one locking feature, the at least one locking feature configured to be received by the locking system, and wherein the step of seating the bioprosthetic valve to the abutment ring includes rotating the holder in the clockwise direction to an engaged position and in a counter-clockwise direction to a disengage position.

Figure 9F:
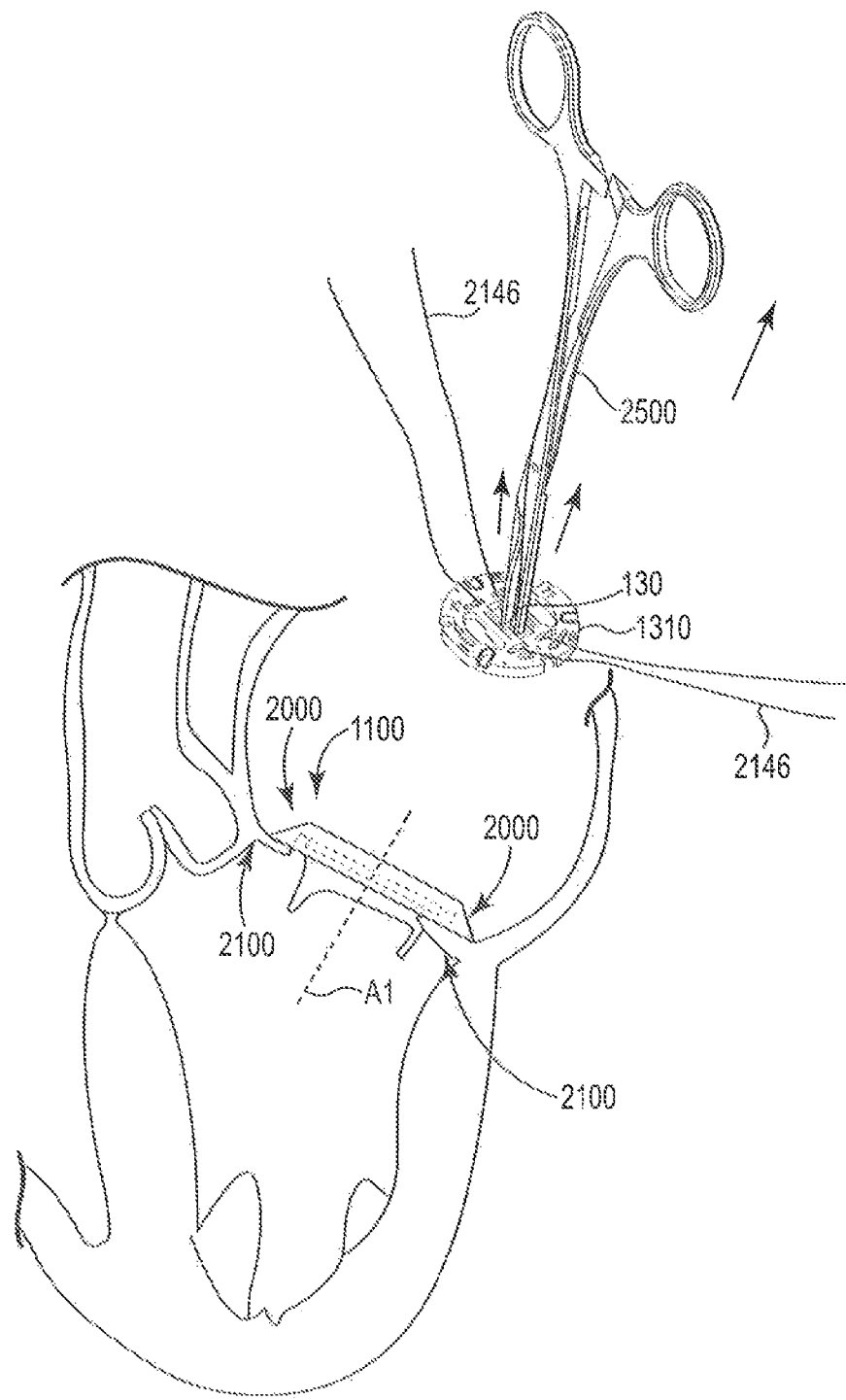
FIG. 9F illustrates removal of a holder according to an implantation procedure of the removable bioprosthetic heart valve assembly, according to some embodiments described in the disclosure.

After seating of the valve, the holder is removed. Sutures (refer to sutures 170, 172, and 174 of FIG. 4) may then be cut to detach and remove holder 1310. The MICS forceps, which remains coupled to the central pin 130, may then be used to remove holder 1310 as shown in FIG. 9F. While holder 1310 is removed from the patient upon completion of the valve implantation, abutment ring 1050 and valve 1320 remain in the patient.

Figure 10:
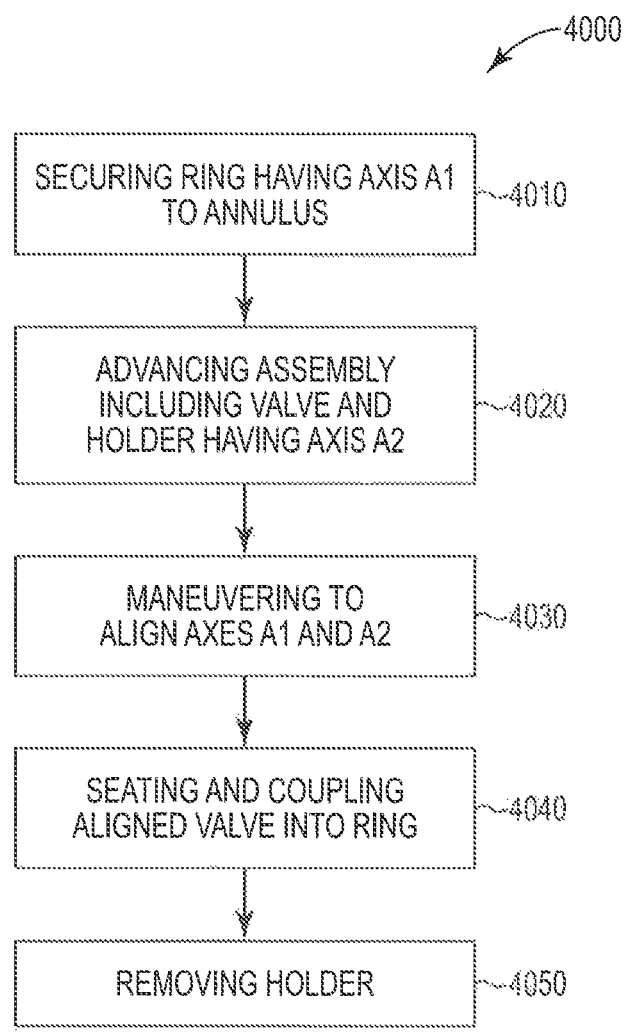
FIG. 10 is a flow chart illustrating a method of implanting a multiple component heart valve prosthesis, according to some embodiments described in the disclosure.

FIG. 10 is a flow chart illustrating method 4000 according to some embodiments. Step 4010 includes securing an abutment ring having a first axis to a patient's annulus. Step 4020 includes advancing a removable bioprosthetic heart valve assembly adjacent to the abutment ring, the removable bioprosthetic heart valve assembly comprising a bioprosthetic valve for coupling to the abutment ring and a holder detachably coupled to the bioprosthetic valve. The holder having a first surface, a second axis perpendicular to the first surface, and a maneuvering system for aligning the first axis and the second axis. Step 4030 includes maneuvering the maneuvering system to align the first axis and the second axis. Step 4040 includes seating the bioprosthetic valve by further advancing the removable bioprosthetic heart valve assembly into the abutment ring and coupling the bioprosthetic valve to the abutment ring. Step 4050 includes removing the holder.

In other embodiments, multiple component heart valve prosthesis 280, referring again to FIG. 1, for implantation at a heart valve annulus location of a patient's heart is disclosed. Heart valve prosthesis 280 comprises: abutment ring 50 configured for attachment at the heart valve annulus location 30, the abutment ring having a first axis A1; and removable bioprosthetic heart valve assembly 250 comprising: bioprosthetic valve 200 configured for coupling to the abutment ring 50; and, holder 100 detachably coupled to the bioprosthetic valve 200. Holder 100 includes: first surface 110 and a second axis A2 perpendicular to the first surface; and, and maneuvering system 120 for aligning the first axis and the second axis (A1 and A2). The maneuvering system includes: central pin 130 pivotable relative to holder 100 and rotatable with holder 100, wherein the second axis A2 passes through central pin 130; and, a first threadable arcuate bore 140 and a second threadable arcuate bore 150, each bore having first and second openings disposed at first surface 110 and first and second threads (146, 156) therethrough, for tilting the first surface and aligning the first axis and the second axis (A1 and A2). In some embodiments, the multiple component heart valve prosthesis further comprises a detachable fit joint having a proximal end and a distal end, the proximal end configured for coupling to the holder and the distal end configured for coupling to an elongated handle.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantation accessory for placement at a heart valve annulus location of a patient's heart, the annulus having a first axis, the implantation accessory comprising:
   a first surface;
   a second axis perpendicular to the first surface; and
   a maneuvering system for aligning the first axis and the second axis, wherein the maneuvering system includes a first threadable bore and a second threadable bore, each bore having first and second openings disposed at the first surface, and the first threadable bore and the second threadable bore are configured to include a first thread and a second thread therethrough, respectively, for tilting the first surface and aligning the first axis and the second axis.

2. The implantation accessory of claim 1, wherein the maneuvering system includes a central pin pivotable relative to the first surface, and wherein the second axis is orthogonal to the central pin.

3. The implantation accessory of claim 2, wherein the central pin is attachable to a minimally invasive cardiothoracic surgery (MICS) forceps.

4. The implantation accessory of claim 1, wherein the implantation accessory is configured to size the annulus.

5. The implantation accessory of claim 1, wherein the implantation accessory is configured to implant a removable bioprosthetic heart valve assembly.

6. The implantation accessory of claim 1, wherein the implantation accessory is configured to implant a removable mechanical heart valve assembly.

7. The implantation accessory of claim 6, wherein the implantation accessory is configured to position a plurality of leaflets of the removable mechanical heart valve assembly.

8. A removable bioprosthetic heart valve assembly for implantation into an abutment ring attached at a heart valve annulus location of a patient's heart, the abutment ring having a first axis, the removable bioprosthetic heart valve assembly comprising:
   a bioprosthetic valve for coupling to the abutment ring; and
   a holder detachably coupled to the bioprosthetic valve, the holder having:

a first surface;
a second axis perpendicular to the first surface; and
a maneuvering system for aligning the first axis and the second axis, wherein the maneuvering system includes a central pin pivotable relative to the holder, wherein the second axis is orthogonal to the central pin and the central pin is attachable to a minimally invasive cardiothoracic surgery (MICS) forceps, and wherein the maneuvering system includes a first threadable arcuate bore and a second threadable arcuate bore, each bore having first and second openings disposed at the first surface.

9. The removable bioprosthetic heart valve assembly of claim 8, wherein the central pin is further rotatable with the holder in a first clockwise direction and in a second counter-clockwise direction.

10. The removable bioprosthetic heart valve assembly of claim 8, wherein the holder is sized according to patient valve requirements.

11. The removable bioprosthetic heart valve assembly of claim 8, wherein the first threadable arcuate bore and the second threadable arcuate bore include a first thread and a second thread therethrough, respectively, for tilting the first surface and aligning the first axis and the second axis.

12. The removable bioprosthetic heart valve assembly of claim 8, further comprising a detachable fit joint having a proximal end and a distal end, the proximal end configured for coupling to the holder and the distal end configured for coupling to an elongated handle.

13. The removable bioprosthetic heart valve assembly of claim 8, further comprising the abutment ring, wherein the abutment ring includes a locking system and the bioprosthetic valve includes at least one locking feature, the at least one locking feature configured to be received by the locking system.

14. The removable bioprosthetic heart valve assembly of claim 13, wherein the locking system comprises at least one channel configured to accept the at least one locking feature of the bioprosthetic valve such that the holder can be rotated relative to the abutment ring to at least a first engaged position and a second disengaged position.

15. The removable bioprosthetic heart valve assembly of claim 14, wherein the maneuvering system includes a central pin rotatable with the holder relative to the abutment ring to rotate the holder in a clockwise direction to the engaged position and in a counter-clockwise direction to the disengaged position.

16. A removable bioprosthetic heart valve assembly for implantation at a heart valve annulus location of a patient's heart, the removable bioprosthetic heart valve assembly comprising:
an abutment ring attachable at the heart valve annulus location of the patient's heart, the abutment ring having a first axis, and wherein the abutment ring includes a locking system;
a bioprosthetic valve for coupling to the abutment ring, wherein the bioprosthetic valve includes at least one locking feature configured to be received by the locking system; and
a holder detachably coupled to the bioprosthetic valve, the holder having:
a first surface;
a second axis perpendicular to the first surface; and
a maneuvering system for aligning the first axis and the second axis, wherein the maneuvering system includes a central pin pivotable relative to the holder, and wherein the second axis is orthogonal to the central pin and the central pin is attachable to a minimally invasive cardiothoracic surgery (MICS) forceps.

17. The removable bioprosthetic heart valve assembly of claim 16, wherein the locking system comprises at least one channel configured to accept the at least one locking feature of the bioprosthetic valve such that the holder can be rotated relative to the abutment ring to at least a first engaged position and a second disengaged position.

18. The removable bioprosthetic heart valve assembly of claim 17, wherein the maneuvering system includes a central pin rotatable with the holder relative to the abutment ring to rotate the holder in a clockwise direction to the engaged position and in a counter-clockwise direction to the disengaged position.

19. The removable bioprosthetic heart valve assembly of claim 16, wherein the central pin is further rotatable with the holder in a first clockwise direction and in a second counterclockwise direction.

20. The removable bioprosthetic heart valve assembly of claim 16, wherein the maneuvering system includes a first threadable bore and a second threadable bore, the first and second threadable bores including a first thread and a second thread therethrough, respectively, for tilting the first surface and aligning the first axis and the second axis.

\* \* \* \* \*